US007964561B2

(12) United States Patent
Garigapati et al.

(10) Patent No.: US 7,964,561 B2
(45) **Date of Patent: *Jun. 21, 2011**

(54) PROTEIN FORMULATIONS FOR USE AT ELEVATED TEMPERATURES

(75) Inventors: Venkata Garigapati, Southborough, MA (US); Dongling Su, Dorchester, MA (US); Julius Lopez, Dorchester, MA (US)

(73) Assignee: Advanced Technologies and Regenerative Medicine, LLC, Raynham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/695,357

(22) Filed: Jan. 28, 2010

(65) Prior Publication Data

US 2010/0130730 A1 May 27, 2010

Related U.S. Application Data

(62) Division of application No. 12/145,016, filed on Jun. 24, 2008, now Pat. No. 7,678,764.

(60) Provisional application No. 60/947,092, filed on Jun. 29, 2007.

(51) Int. Cl.

| | |
|---|---|
| ***A61K 38/16*** | (2006.01) |
| ***A61K 38/17*** | (2006.01) |
| ***A61K 38/18*** | (2006.01) |
| ***C07H 1/00*** | (2006.01) |

(52) U.S. Cl. .......... 514/8.9; 514/8.8; 514/7.6; 514/16.7; 514/16.8; 514/16.9; 514/17.1; 536/123.1

(58) Field of Classification Search ........................ None
See application file for complete search history.

(56) References Cited

U.S. PATENT DOCUMENTS

| | | | |
|---|---|---|---|
| 2,931,802 | A | 4/1960 | Touey |
| 4,120,810 | A | 10/1978 | Palmer |
| 4,891,319 | A | 1/1990 | Roser |
| 5,011,691 | A | 4/1991 | Oppermann |
| 5,013,649 | A | 5/1991 | Wang |
| 5,202,311 | A | 4/1993 | Folkman |
| 5,231,169 | A | 7/1993 | Constantz |
| 5,266,683 | A | 11/1993 | Oppermann |
| 5,318,898 | A | 6/1994 | Israel |
| 5,385,887 | A | 1/1995 | Yim |
| 5,411,941 | A | 5/1995 | Grinna |
| 5,455,231 | A | 10/1995 | Constantz |
| 5,516,654 | A | 5/1996 | Israel |
| 5,658,882 | A | 8/1997 | Celeste |
| 5,747,058 | A | 5/1998 | Tipton |
| 5,770,700 | A | 6/1998 | Webb |

(Continued)

FOREIGN PATENT DOCUMENTS

EP 955313 A1 11/1999

(Continued)

OTHER PUBLICATIONS

PCT Search Report dated Jul. 10, 2008 for application No. PCT/US2008/068007.

(Continued)

*Primary Examiner* — Elizabeth C Kemmerer

(57) ABSTRACT

Liquid formulations of bone morphogenetic proteins are provided for prolonged use at elevated temperatures. More specifically, the invention relates to liquid formulations comprising rhGDF-5, trehalose, and one or more biocompatible excipients that provide stability to the protein for at least 30 days at temperatures up to body temperature.

12 Claims, 11 Drawing Sheets

Biological activity of formulation # 18 at time zero and after 60 days at 37° C compared with freshly prepared standard GDF-5 solution.

U.S. PATENT DOCUMENTS

| | | | |
|---|---|---|---|
| 5,776,193 | A | 7/1998 | Kwan |
| 5,801,014 | A | 9/1998 | Lee |
| 5,804,557 | A | 9/1998 | Cleland |
| 5,866,165 | A | 2/1999 | Liu |
| 5,955,448 | A | 9/1999 | Colaco |
| 5,968,542 | A | 10/1999 | Tipton |
| 5,972,385 | A | 10/1999 | Liu |
| 5,985,320 | A | 11/1999 | Edwards |
| 6,051,558 | A | 4/2000 | Burns |
| 6,071,428 | A | 6/2000 | Franks |
| 6,165,981 | A | 12/2000 | Flaa |
| 6,171,584 | B1 | 1/2001 | Hotten |
| 6,171,586 | B1 | 1/2001 | Lam |
| 6,187,742 | B1 | 2/2001 | Wozney |
| 6,207,718 | B1 | 3/2001 | Papadimitriou |
| 6,281,195 | B1 | 8/2001 | Rueger |
| 6,284,872 | B1 | 9/2001 | Celeste |
| 6,288,043 | B1 | 9/2001 | Spiro |
| 6,340,369 | B1 | 1/2002 | Ferree |
| 6,344,058 | B1 | 2/2002 | Ferree |
| 6,352,557 | B1 | 3/2002 | Ferree |
| 6,407,060 | B1 | 6/2002 | Charette |
| 6,419,702 | B1 | 7/2002 | Ferree |
| 6,454,804 | B1 | 9/2002 | Ferree |
| 6,551,801 | B1 | 4/2003 | Andou |
| 6,645,247 | B2 | 11/2003 | Ferree |
| 6,648,918 | B2 | 11/2003 | Ferree |
| 6,648,919 | B2 | 11/2003 | Ferree |
| 6,648,920 | B2 | 11/2003 | Ferree |
| 6,656,492 | B2 | 12/2003 | Kajiyama |
| RE38,385 | E | 1/2004 | Franks et al. |
| 6,685,695 | B2 | 2/2004 | Ferree |
| 6,719,968 | B2 | 4/2004 | Celeste |
| 6,723,170 | B2 | 4/2004 | Ohashi |
| 6,755,863 | B2 | 6/2004 | Ferree |
| 6,764,994 | B1 | 7/2004 | Hotten |
| 6,780,324 | B2 | 8/2004 | Le Garrec |
| 6,911,411 | B2 | 6/2005 | Cox |
| 6,936,582 | B1 | 8/2005 | Charette |
| 6,991,790 | B1 | 1/2006 | Lam |
| 6,992,065 | B2 | 1/2006 | Okumu |
| 7,060,268 | B2 | 6/2006 | Andya |
| RE39,497 | E | 2/2007 | Franks et al. |
| 7,235,527 | B2 | 6/2007 | Makishima |
| 7,318,840 | B2 | 1/2008 | McKay |
| 7,323,445 | B2 | 1/2008 | Zhang |
| 7,375,077 | B2 | 5/2008 | Mao |
| 7,435,260 | B2 | 10/2008 | Ferree |
| 7,572,440 | B2 | 8/2009 | Vukicevic |
| 7,678,764 | B2 * | 3/2010 | Garigapati et al. ............... 514/2 |
| 2001/0024823 | A1 | 9/2001 | Vukicevic |
| 2002/0032155 | A1 | 3/2002 | Ferree |
| 2002/0128718 | A1 | 9/2002 | Ferree |
| 2002/0165542 | A1 | 11/2002 | Ferree |
| 2002/0173770 | A1 | 11/2002 | Flory |
| 2003/0026788 | A1 | 2/2003 | Ferree |
| 2003/0185812 | A1 | 10/2003 | Ferree |
| 2003/0192554 | A1 | 10/2003 | Ferree |
| 2004/0022771 | A1 | 2/2004 | Ferree |
| 2004/0024471 | A1 | 2/2004 | Ferree |
| 2004/0028733 | A1 | 2/2004 | Tracy |
| 2004/0132653 | A1 | 7/2004 | Ichikawa |
| 2004/0146923 | A1 | 7/2004 | Celeste |
| 2004/0197324 | A1 | 10/2004 | Liu |
| 2005/0069571 | A1 | 3/2005 | Slivka |
| 2005/0119754 | A1 | 6/2005 | Trieu |
| 2005/0191248 | A1 | 9/2005 | Hunter |
| 2006/0024346 | A1 | 2/2006 | Brody |
| 2006/0088565 | A1 | 4/2006 | Kohnert |
| 2006/0121113 | A1 | 6/2006 | Bartholomaeus |
| 2006/0223120 | A1 | 10/2006 | Kim |
| 2006/0286171 | A1 | 12/2006 | Zhou |
| 2006/0286289 | A1 | 12/2006 | Prajapati |
| 2006/0287676 | A1 | 12/2006 | Prajapati |
| 2007/0053871 | A1 | 3/2007 | Li et al. |
| 2007/0098756 | A1 | 5/2007 | Behnam |
| 2007/0172479 | A1 | 7/2007 | Warne et al. |
| 2007/0178159 | A1 | 8/2007 | Chen |
| 2008/0098614 | A1 | 5/2008 | Tchessalov |
| 2008/0147077 | A1 | 6/2008 | Garigapati et al. |
| 2008/0234727 | A1 | 9/2008 | Garigapati |
| 2008/0311078 | A1 | 12/2008 | Gokarn |
| 2009/0004048 | A1 | 1/2009 | Elliott |
| 2009/0030483 | A1 | 1/2009 | Risi |
| 2009/0043078 | A1 | 2/2009 | Daniel |
| 2009/0048412 | A1 | 2/2009 | Soula |
| 2009/0060976 | A1 | 3/2009 | Rueger |
| 2009/0099089 | A1 | 4/2009 | Zhang |
| 2009/0259023 | A1 | 10/2009 | Su |
| 2009/0286764 | A1 | 11/2009 | Kipp |
| 2009/0291062 | A1 | 11/2009 | Fraunhofer |
| 2010/0015230 | A1 | 1/2010 | Ron |
| 2010/0041870 | A1 | 2/2010 | Tchessalov |
| 2010/0144631 | A1 | 6/2010 | Ron |
| 2010/0255100 | A1 | 10/2010 | Margolin |

FOREIGN PATENT DOCUMENTS

| | | | |
|---|---|---|---|
| EP | 957943 | B1 | 5/2003 |
| EP | 1350525 | A2 | 10/2003 |
| EP | 1448246 | A1 | 8/2004 |
| EP | 1462126 | A1 | 9/2004 |
| EP | 1274459 | B1 | 11/2005 |
| EP | 1604693 | A1 | 12/2005 |
| EP | 1604963 | A2 | 12/2005 |
| EP | 0955313 | | 5/2006 |
| EP | 955313 | B1 | 5/2006 |
| EP | 1915986 | A1 | 4/2008 |
| EP | 1932519 | A1 | 6/2008 |
| EP | 957943 | B2 | 11/2008 |
| WO | WO 8800205 | A1 | 1/1988 |
| WO | WO 9011366 | A1 | 10/1990 |
| WO | WO 9118098 | A1 | 11/1991 |
| WO | WO 9200382 | A1 | 1/1992 |
| WO | WO 9309229 | A1 | 5/1993 |
| WO | WO 9316099 | A2 | 8/1993 |
| WO | WO 9410203 | A2 | 5/1994 |
| WO | WO 9415949 | A1 | 7/1994 |
| WO | WO 9415965 | A1 | 7/1994 |
| WO | WO 9415966 | A1 | 7/1994 |
| WO | WO 9421681 | A1 | 9/1994 |
| WO | WO 9426892 | A1 | 11/1994 |
| WO | WO 9426893 | A1 | 11/1994 |
| WO | WO 9501801 | A1 | 1/1995 |
| WO | WO 95/04819 | | 2/1995 |
| WO | WO 9510539 | A1 | 4/1995 |
| WO | WO 9510802 | A1 | 4/1995 |
| WO | WO 9516035 | A2 | 6/1995 |
| WO | WO 9533830 | A1 | 12/1995 |
| WO | WO 9601316 | A1 | 1/1996 |
| WO | WO 9601845 | A1 | 1/1996 |
| WO | WO 96/14335 | | 5/1996 |
| WO | WO 9636710 | A1 | 11/1996 |
| WO | WO 0178683 | A2 | 10/2001 |
| WO | WO 03000282 | A1 | 1/2003 |
| WO | WO 03030923 | A1 | 4/2003 |
| WO | WO 03043673 | A1 | 5/2003 |
| WO | WO 03066120 | A1 | 8/2003 |
| WO | WO 2004037265 | A1 | 5/2004 |
| WO | WO 2004052336 | A2 | 6/2004 |
| WO | WO 2005060989 | A1 | 7/2005 |
| WO | WO 2005100399 | A2 | 10/2005 |
| WO | WO 2005107765 | A2 | 11/2005 |
| WO | WO 2005115438 | A1 | 12/2005 |
| WO | WO 2006/138099 | A2 | 12/2006 |
| WO | WO 2006138099 | A2 | 12/2006 |
| WO | WO 2006138181 | A2 | 12/2006 |
| WO | WO 2007025441 | A1 | 3/2007 |
| WO | WO 2008009419 | A1 | 1/2008 |
| WO | WO 2008045498 | A1 | 4/2008 |
| WO | WO 2008049588 | A1 | 5/2008 |
| WO | WO 2008079672 | A2 | 7/2008 |
| WO | WO 2008082563 | A2 | 7/2008 |
| WO | WO 2008099190 | A2 | 8/2008 |
| WO | WO 2008099198 | A2 | 8/2008 |
| WO | WO 2008143867 | A1 | 11/2008 |
| WO | WO 2009006097 | A1 | 1/2009 |
| WO | WO 2009006301 | A2 | 1/2009 |

| | | | |
|---|---|---|---|
| WO | WO 2009015736 A1 | 2/2009 |
| WO | WO 2009016131 A1 | 2/2009 |
| WO | WO 2009016333 A1 | 2/2009 |
| WO | WO 2009020744 A1 | 2/2009 |

OTHER PUBLICATIONS

Triantfilou, et al.*Nature Immunology* 2, 338-345 (2001).
Massague, et al. *Annual Review of Cell Biology* 6:957 (1990).
Sampath, et al. *Journal of Biological Chemistry* 265:13198 (1990).
Celeste et al. *PNAS* 87:9843-47 (1990).
Arakawa et al., *Advanced Drug Delivery Reviews*, 46, 307-326 (2001).
Wang, et al., *International Journal of Pharmaceutics* 185, 129-188 (1999).
Crowe, et al., *Cryobiology* 43, 89-105 (2001).
Higashiyama, *Pure Appl. Chem.* 74, 1263-1269 (2002).
Nakamoto, et al. in *Cell Mol Life Sci.* Feb; 64(3): 294-306 (2007).
Letter from Keith E. Gilman of Lerner David Littenberg Krumholz & Mentlik LLP, dated Sep. 13, 2010 regarding Johnson & Johnson U.S. Publication No. 2008/0147077A1.
EP Search Report 07254571.8, May 8, 2008.
EP Search Report for App No. PCT/US2009/039925 dated Aug. 10, 2009.
Dayhoffel et al., A Model of Evolutionary Change in Proteins, Atlas of Protein Sequence and Structure, vol. Suppl 3., pp. 354-352 1978.
Wozney et al., Novel Regulators of Bone Formation: Molecular Clones and Activities, Science 242:1528-1534, 1988.
Padgett et al., A transcript from a *Drosophila*pattern gene predicts a protein homologous to the transforming growth factor-B family, Nature 325:81-84 (1987).
Needleman et al., A General Method Applicable to the Search for Similarities in the Amino Acid Sequence of Two Proteins, J. Mol. Biol. 48:443-453 (1970).
Storm et al., Limb alterations in brachypodism mice due to mutations in a new member of the TGFβ-superfamily, Nature 368:639-643 1994.
Takao et al., Identification of Rate Bone Morphogenetic Protein-3b (BMP-3b), a New Member of BMP-3, Biochemical and Biophysical Research Communications, 219:656-662, 1996.
Basler et al., Control of Cell Pattern in the Neural Tube: Regulation of Cell Differentiation by dorsalin-1, a Novel TGFβ Family Member, Cell 73:687-702, 1993.
Weeks, A Maternal mRNA Localized to the Vegetal Hemisphere in Zenopus Eggs Codes for a Growth Factor Related to TGF-β, Cell, Vo. 51, 861-867, 1987.
Arakawa et al., Pharmaceutical Research "Protein-Solvent Interactions in Pharmaceutical Formulations", vol. 8, No. 3, 1991, pp. 285-291.
Brus, C. et. al., "Stabilization of Oligonucleotide-Polyethylenimine Complexes by Freeze-Drying: Physicochemical and Biological Characterization". Journal of Controlled Release, Feb. 20, 2004, vol. 95, Issue 1, pp. 119-131.
Cheng, Hongwei. "Osteogenic Activity of the Fourteen Types of Human Bone Morphogenic Proteins", Journal Bone Joint Surgery Am. 85A, 2003, pp. 1544-1552.
Costantino, Henry R. et. al., "Effect of Excipients on the Stability and Structure of Lyophilized Recombinant Human Growth Hormone", Journal of Pharmaceutical Sciences, 1998, vol. 87, Issue 11, pp. 1412-1420.
Crowe, J., "Stabilization of Dry Phospholipid Bilayers and Proteins by Sugars", Biochem. J., 1987, 242, pp. 1-10.
Gloger, O., "Lyoprotection of Aviscumine with Low Molecular Weight Dextrans", International Journal of Pharmaceutics, Jul. 9, 2003, vol. 260, Issue 1, pp. 59-68.
Goodnough, M C, et. al., "Stabilization of Botulinum Toxin Type A During Lyophilization", Applied Environmental Microbiology, 1992, vol. 58, Issue 10, pp. 3426-3428.
Gupta Intl J Pharm 318 (2006) 163-173.
Honda et al. Jouranl of Bioscience and Bioengineering 89(6), 582-589 (2000).
Lories, Rik, J. U., "Bone Morphogenetic Protein Signaling in Joint Homeostasis and Disease", Cytokine Growth Factor Review, vol. 16, Issue 3, 2005, pp. 287-298.
Lyons, K et. al., "Vgr-1, a Mammalian Gene Related to Xenopus Vg-1, is a M Member of the Transforming Growth Factor Beta Gene Superfamily", Proceedings of the National Academy of Science, 1989, vol. 86, Issue 12, pp. 4554-4558.
Massague, J., "The Transforming Growth Factor-beta Family", Annual Review of Cell Biology, Nov. 1990, vol. 6, pp. 597-641.
Ozkaynak et. at., "OP-1 cDNA Encodes an Osteogenic Protein in the TGF-Beta Family". EMBO Journal, 1990, vol. 9, Issue 7, pp. 2085-2093.
Ramos et. al., "Stabilization of Enzymes Against Thermal Stress and Freeze-Drying by Mannosylglycerate", Appl. Envir. Microiol. 1997, vol. 63, Issue 10, pp. 4020-4025.
Ruppert, et al. Eur J Biochem 237, 295-302 (1996).
Wharton, Ka et. al., "Drosophila 60A Gene, Another Transforming Growth Factor Beta Family Member, is Closely Related to Human Bone Morphogenetic Proteins", Proceedings of the National Academy of Science, 1991, vol. 88, Issue 20, pp. 9214-9218.
Yancey, Paul, "Organic Osmolytes as Compatible, Metabolic and Counteracting Cytoprotectants in High Osmolarity and Other Stresses" Journal of Experimental Biology, 2005, vol. 208, pp. 2819-2830.
Von Heijne, Nucleic Acids Research 14:4683-4691 (1986).
Rickert et al., Growth Factors, 19, 2001, 115-123.
Schmidmaier, J. Biomedical Materials Res Appl Biomat, 58, 449-455, 2001.
Rothenberger, Surgical Infection Society Journal Supp, Dec. 2002, p. 579-87.
Mangram, Infection control and Hospital Epidemiology, 1999, 20(40, 247-280).
Lee et al., Proc. Natl. Acad. Sci 88:4250-4254 1991.
Mazzocca AAOS Abstract #338 2005.
Wright 50th ORS #1234 2004.
Peterson 51st ORS #0076 2005.

* cited by examiner rp-HPLC of formulation 18 after 30 days at 37° C showing preservation of protein rp-HPLC of formulation 37 after 30 days at 37° C showing preservation of protein rp-HPLC of formulation 35 after 30 days at 37° C showing degradation of protein rp-HPLC of formulation 21 after 60 days at 37° C showing preservation of protein SEC of formulation 12 after 12 days at 37° C showing preservation of protein SEC of formulation 18 after 30 days at 37° C showing preservation of protein Sample of protein in 60% w/v trehalose alone at day 14 showing degradation of protein, as evidenced by 75% preservation of main peak, with presence of additional peaks.

Chromatograph of GDF-5 reference standard (no formulation)

Biological activity of formulation # 18 at time zero and after 60 days at 37° C compared with freshly prepared standard GDF-5 solution.

PROTEIN FORMULATIONS FOR USE AT ELEVATED TEMPERATURES

RELATED APPLICATION

This application is a divisional application of U.S. patent application Ser. No. 12/145,016, filed on Jun. 24, 2008, which is now U.S. Pat. No. 7,678,764, which claims priority from U.S. Patent Application No. 60/947,092, filed on, Jun. 29, 2007.

FIELD OF THE INVENTION

The invention relates to liquid formulations of bone morphogenetic proteins for prolonged use at elevated temperatures. More specifically, the invention relates to liquid formulations comprising rhGDF-5, trehalose, and one or more biocompatible excipients to provide formulations that are stable at temperatures up to 37° C. for 30 days or longer.

BACKGROUND OF THE INVENTION

GDF-5 is a member of the Bone Morphogenetic Proteins (BMP), which is a subclass of the TGF-β superfamily of proteins. GDF-5 includes several variants and mutants, including mGDF-5 first isolated from the mouse by Lee (U.S. Pat. No. 5,801,014). Other variants include MP52 (WO 95/04819), which is a human form of GDF-5, also known as hGDF-5 and LAP-4 (Triantfilou, et al. *Nature Immunology* 2, 338-345 (2001)); also CDMP-1, an allelic protein variant of hGDF-5 (WO 96/14335); also rhGDF-5, the recombinant human form manufactured in bacteria (EP 0955313); also rhGDF-5-Ala83, a monomeric variant of rhGDF-5; also BMP-14, a collective term for hGDF-5/CDMP-1 like proteins; also Radotermin, the international name designated by the World Health Organization; also HMW MP52's, high molecular weight protein variants of MP52; also C465A, a monomeric version wherein the cysteine residue responsible for the intermolecular cross-link is substituted with alanine; also other active single amino acid substitution mutants including N445T, L441P, R438L, and R438K. For the purposes of this application the term "GDF-5" is meant to include all variants and mutants of the protein, and rhGDF-5 is the exemplary member having 119 amino acids.

All members of the BMP family share common structural features including a carboxy terminal active domain and share a highly conserved pattern of cysteine residues that create 3 intramolecular disulfide bonds and one intermolecular disulfide bond. The active form can be either a disulfide-bonded homodimer of a single family member or a heterodimer of two different members (see Massague, et al. *Annual Review of Cell Biology* 6:957 (1990); Sampath, et al. *Journal of Biological Chemistry* 265:13198 (1990); Celeste et al. *PNAS* 87:9843-47 (1990); U.S. Pat. No. 5,011,691, and U.S. Pat. No. 5,266,683). The proper folding of the protein and formation of these disulfide bonds are essential to biological functioning, and misfolding leads to inactive aggregates and cleaved fragments.

The degradation and stabilization of proteins in general has been well described in the literature, and the use of excipients such as dextran, lactose, sorbitol, mannitol, sucrose and trehalose as cryoprotectants and osmoregulators are well documented (see for example reviews of protein stability by Arakawa et al., *Advanced Drug Delivery Reviews,* 46, 307-326 (2001), Wang, et al., *International Journal of Pharmaceutics* 185, 129-188 (1999), and on trehalose by Crowe, et al., *Cryobiology* 43, 89-105 (2001)). The use of excipients to protect lyophilized formulations of GDF-5 has also been described in USPAP 20040132653 by Ichikawa, et al., USPAP 20060286171 by Zhou, et al., and U.S. Patent Application Ser. No. 60/870,032 by Garigapati, et al. Lyophilization is a process that is commonly used and is comprised of freeze-drying a sample to remove water to yield a solid cake for storage, which can then be rehydrated at the time of use. For proteins such as GDF-5, the freezing, drying, and rehydration with water all represent separate insults and challenges to the structure and integrity of the protein.

The use of trehalose as a bulking agent in formulations for stabilizing solutions of the protein troponin has been described by Flaa, et al., in U.S. Pat. No. 6,165,981. The stabilization of antibodies using trehalose have also been described, such as by Lam, et al., in U.S. Pat. Nos. 6,171,586 and 6,991,790. These proteins share little structural similarity with GDF-5, and the use of formulations that are successful for other proteins are not necessarily predictable for use in stabilizing GDF-5.

In contrast, the preparation of a liquid solution of GDF-5 that is stable for prolonged periods of time at elevated temperatures, such as at room temperature, or even at body temperature, present a separate set of challenges that are distinctly different from those of freezing, drying, and rehydrating, as encountered in lyophilization and reconstitution. No longer are the biochemical insults to the protein structure derived from the removal of water, the crystallization of excipients, and the changes in the local microenvironment of the protein chains, their hydrogen and sulfide bonds, and their tertiary structure, but rather the challenge is from increased thermodynamic motion. This leads to an increased rate of oxidation, deamidation, hydrolysis, and cleavage of the amino acids of the protein as the predominant deactivation mechanisms, producing small fragments and an inactive parent molecule, with a lesser amount of aggregation than is commonly observed in lyophilization processes. Reversed phase high performance liquid chromatography (rp-HPLC) and size exclusion chromatography (SEC) appear to be more reliable indicators of protein purity and stability than other methods, such as electrophoresis.

Thus, the strategy and chemistry needed to stabilize a protein such as GDF-5 for a liquid solution at room temperature or above may require a different formulation than one for lyophilization. GDF-5 is not stable in solution for prolonged periods of time at 2-8° C., and is typically stored at temperatures between −60 to −80° C. GDF-5 is not soluble at neutral pH and is typically solubilized in acidic solutions, thereby increasing the potential for acid hydrolysis.

In view of the above-mentioned limitations and complications of preparing a stable GDF-5 liquid formulation for prolonged storage and use at elevated temperatures, new and effective formulations are needed.

SUMMARY OF THE INVENTION

The invention is a liquid protein formulation. The formulation comprises a BMP, at least a 50% w/v solution of trehalose, and at least one additional excipient selected from the group consisting of an amino acid, a trialkylammonium salt, a heat shock protein, a betaine, taurine, raffinose, myo-inositol, and potassium aspartate in an amount sufficient to stabilize the BMP as evidenced by retention of at least 80% of the main chromatography peak for at least 30 days storage at temperatures up to 37° C.

In another embodiment, the invention is a method of stabilizing a BMP solution having a BMP, at least a 50% w/v solution of trehalose, and at least one additional excipient selected from the group consisting of an amino acid, a trialkylammonium salt, a heat shock protein, a betaine, taurine, raffinose, myo-inositol, and potassium aspartate.

The protein formulations of the present invention can be used in all applications where the storage and use of bone morphogenetic proteins is desired. The storage and use of bone morphogenetic proteins at room temperature or body temperature present useful applications of these formulations. Table 1 shows a summary of the different formulations tested and the results.

TABLE 1

Summary of Formulations and Data

| Formulation # | SEC % Main Peak Day 30, 37° C. | rp-HPLC % Main Peak Day 30, 37° C. | rp-HPLC % Main Peak Day 60, 37° C. | pH | Trehalose w/v % | Taurine wt % | Raffinose wt % |
|---|---|---|---|---|---|---|---|
| 1 | | 66 | | 6.8 | 60 | | |
| 2 | | 73 | | 6.6 | 60 | | |
| 3 | | 76 | | 6.3 | 60 | | |
| 4 | | 86 | | 6.1 | 60 | | |
| 5 | | 92 | | 3.1 | 60 | | |
| 6 | | 91 | | 3.2 | 60 | | |
| 7 | | 88 | | 3.0 | 60 | | |
| 8 | | 87 | | 2.9 | 60 | | |
| 9 | | 87 | | 2.9 | 60 | | |
| 10 | | 87 | | 2.7 | 60 | | 3 |
| 11 | | 77 | | 5.8 | 60 | | 3 |
| 12 | | 74 | | 6.0 | 60 | | 3 |
| 13 | | 56 | | 6.4 | 60 | | 3 |
| 14 | | 88 | | 5.0 | 60 | | |
| 15 | | 89 | | 5.4 | 60 | | |
| 16 | | 89 | | 5.8 | 60 | | |
| 17 | | 84 | | 6.0 | 60 | | |
| 18 | 98 | 94 | 76 | 5.6 | 60 | | |
| 19 | 95 | 91 | 88 | 5.3 | 60 | 0.1 | |
| 20 | | 79 | 71 | 3.5 | 60 | 0.1 | |
| 21 | 97 | 92 | 92 | 5.4 | 60 | | |
| 22 | | 76 | 66 | 5.3 | 60 | | |
| 23 | 98 | 93 | 78 | 5.4 | 60 | | |
| 24 | | 82 | 75 | 5.6 | 60 | | |
| 25 | | 62 | 48 | 5.7 | 60 | | |
| 26 | | 66 | 58 | 5.7 | 60 | | |
| 27 | | 65 | 53 | 5.4 | 60 | | |
| 28 | | 83 | 76 | 5.3 | 60 | | |
| 29 | | 68 | 53 | 3.9 | 60 | | |
| 30 | | 78 | 66 | 3.5 | 60 | | |
| 31 | | 76 | 56 | 3.6 | 60 | | |
| 32 | | 80 | 67 | 3.5 | 60 | | |
| 33 | | 56 | 43 | 5.7 | 60 | | |
| 34 | | 87 | 69 | 5.9 | 60 | | |
| 35 | | 59 | 52 | 6.4 | 60 | | |
| 36 | | 72 | 49 | 5.2 | 60 | | |
| 37 | 91 | 94 | 91 | 5.3 | 60 | | |

| Formulation # | Myo-inositol wt % | Betaine wt % | HSP70 wt % | β-Alanine wt % | TMAO wt % | TMA wt % | TEA wt % | L-Proline wt % | Potassium Aspartate wt % |
|---|---|---|---|---|---|---|---|---|---|
| 1 | | | | | 1 | | | | |
| 2 | | | | | 0.5 | | | | |
| 3 | | | | | 0.25 | | | | |
| 4 | | | | | 0.1 | | | | |
| 5 | | | 0.1 | | | | | | |
| 6 | | | 0.2 | | | | | | |
| 7 | | | | | | 1 | | | |
| 8 | | | | | | 2 | | | |
| 9 | | | | | | 5 | | | |
| 10 | 1 | | | | | | | | |
| 11 | 1 | | | | 0.01 | | | | |
| 12 | 1 | | | | 0.25 | | | | |
| 13 | 1 | | | | 0.5 | | | | |
| 14 | | | | 0.25 | | | | | |
| 15 | | | | 0.5 | | | | | |
| 16 | | | | 0.25 | 0.1 | | | | |
| 17 | | | | 0.5 | 0.1 | | | | |
| 18 | | | | 0.5 | | 0.1 | | | |
| 19 | | | | 0.5 | | | | | |
| 20 | | 0.5 | | | | | | | |
| 21 | | | | 0.5 | | | 0.1 | | |
| 22 | | | | 0.5 | | | 0.5 | | |
| 23 | | 0.5 | | | | | 1 | 0.5 | 0.5 |
| 24 | | 0.5 | | 0.5 | | | 0.1 | 0.5 | 0.5 |

TABLE 1-continued

| Summary of Formulations and Data | | | | | | |
|---|---|---|---|---|---|---|
| 25 | 0.5 | 0.5 | | | 0.5 | 0.5 |
| 26 | | 0.5 | | | 0.5 | 0.5 |
| 27 | | 0.5 | | | 0.5 | |
| 28 | 0.5 | | | | 0.5 | 0.5 |
| 29 | 0.5 | | | | 0.5 | |
| 30 | 0.5 | | | | | |
| 31 | | | | | 0.5 | |
| 32 | 0.5 | | | | | |
| 33 | | 1 | | | | |
| 34 | | 2 | | | | |
| 35 | | 5 | | | | |
| 36 | | 0.5 | 0.1 | | | |
| 37 | | 0.5 | | 3 | | |

DETAILED DESCRIPTION

The bone morphogenetic proteins that may be used in the present invention include, but are not limited to, BMP-2, BMP-4, BMP-6, BMP-7, BMP12, and BMP-14, and all variants and mutants thereof The preferred BMP is rhGDF-5, also known as MP52.

Here we provide several formulations that are useful as compositions providing stability of the BMP molecule in aqueous solution at elevated temperatures for prolonged periods of time. For the purposes of the present invention, the terms "room temperature" and "ambient temperature" are understood to be interchangeable and to mean the temperature of an ordinary office or laboratory having a temperature of between approximately 18 to 25° C.; the term "body temperature" means the normal body temperature of humans, being a temperature of approximately 37° C.; the term "refrigerated temperature" means a temperature of between approximately 2 to 8° C.; the term "frozen" means a temperature of between approximately −4° C. to −20° C.

The stability of BMP has been shown by various analytical methods such as rp-HPLC and SEC, and does not rely on vague biological assays for determining the chemical purity of the BMP molecule and thus the performance of the formulation. For the purposes of the present invention, the terms "stability" and "purity" are interchangeable and meant to describe the characterization of a BMP by rp-HPLC or SEC chromatography, and refer to the area under the curve of the main peak as a measure of the preservation of the parent molecule. A biological assay has also been performed to correlate the stability with the biological activity of the BMP (see FIG. 11).

Figure 9:
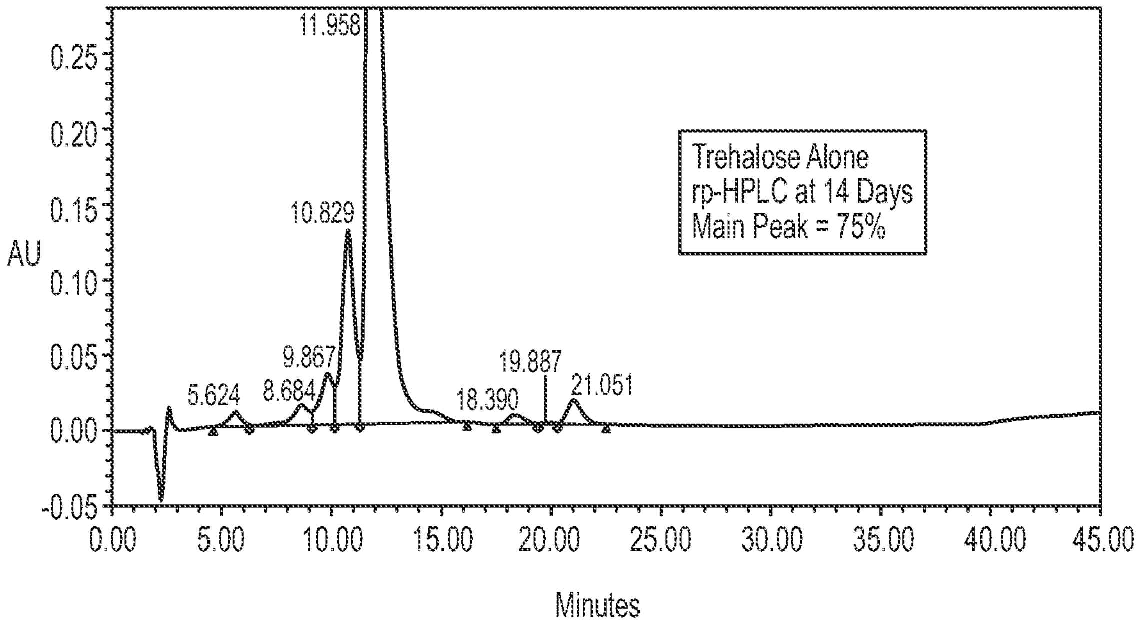
FIG. 9 shows the stability of a GDF-5 sample with 60% w/v trehalose alone by rp-HPLC after 14 days at 37° C. The preservation of the protein is shown to be 75% by the main peak, with the presence of additional peaks indicating degradation.
Figure 10:
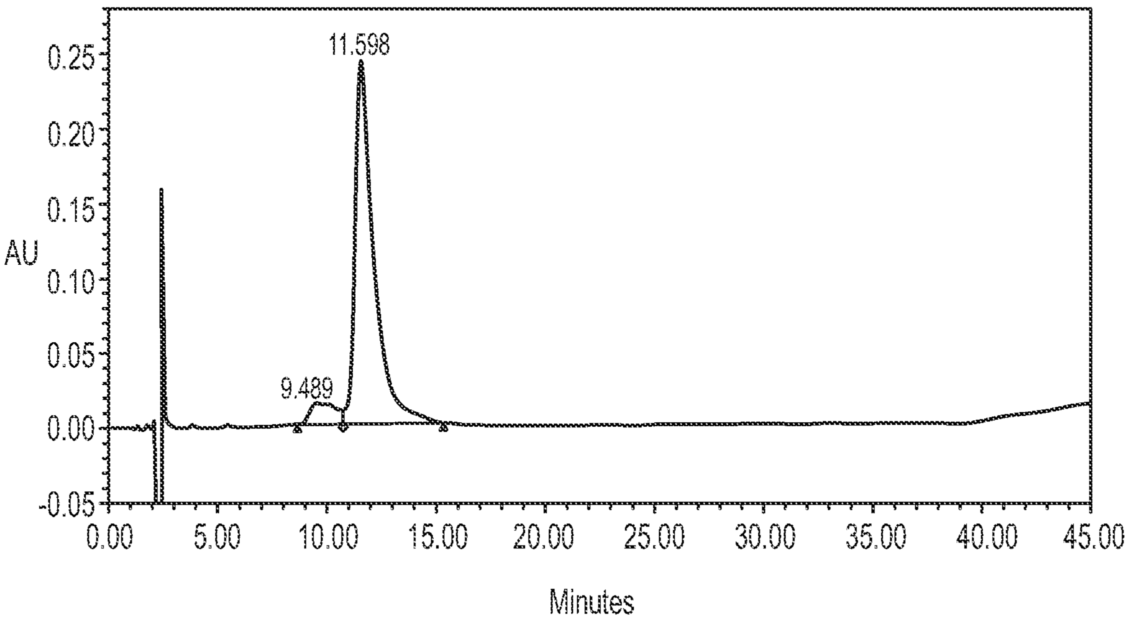
FIG. 10 shows a chromatograph of a GDF-5 reference standard (no formulation)

A formulation of the present invention includes a BMP, at least a 50% w/v solution of trehalose in an acidic solution, and at least one additional excipient selected from the group consisting of an amino acid, a trialkylammonium salt, a heat shock protein, a betaine, taurine, raffinose, myo-inositol, and potassium aspartate. Trehalose is a well-known excipient that provides stability to proteins in solution and in lyophilized formulations, but it is not sufficient in itself to provide prolonged stability to liquid solutions of GDF-5 at body temperature. This is evidenced by the reduction in the main peak and the appearance of additional peaks in the rp-HPLC chromatograph of FIG. 9 after 14 days storage at a temperature of 37° C., as compared to the standard chromatograph shown in FIG. 10.

The solubility of trehalose has been reported to be 68.9 g/100 g $H_2O$ (Higashiyama, *Pure Appl. Chem.* 74, 1263-1269 (2002)). We used trehalose solutions of 50% and 60% w/v and investigated several excipients and combinations thereof to find a formulation that would provide for a stable liquid BMP solution to yield at least 80% retention of the protein purity, as evidenced by the main peak in an rp-HPLC or SEC chromatograph after storage for 30 days or longer at temperatures up to 37° C. After much experimentation, we have found certain combinations of excipients to be of value in meeting this goal. We also attempted to increase the pH of various formulations to minimize the potential for acid hydrolysis and cleavage of the protein. The desired pH range is from about 2.5 to about 7.0, and more preferably from about 4.0 to about 6.0. Lower pH values tend to lead to higher rates of acid hydrolysis of the protein, and higher pH values tend to cause insolubility of the protein. Hydrochloric acid is preferred due to its biocompatibility, and values of 0.5 to about 3 millimolar are preferred, although higher values of up to about 10 millimolar HCl are acceptable. It would be obvious to one of ordinary skill in the art that other biocompatible acids could also be used in the formulations of the present invention.

Trimethylammonium N-Oxide dihydrate (TMAO) was tested in various concentrations in addition to trehalose, and in general found to have deleterious effects on the stability of the protein. While a 0.1% w/v addition of TMAO provided an acceptable 86% retention of the main peak, increasing concentrations of TMAO led to a reduction in protein stability (formulations 1-4). In comparing formulations 15 and 17, both containing a 0.5% w/v content of β-alanine, the addition of 0.1% w/v TMAO reduced the protein stability from 89% to 84%. In other formulations comprising raffinose and myo-inositol, the addition of TMAO also appeared to have a deleterious effect on the protein stability. While a formulation of 3% raffinose and 1% myo-inositol had satisfactory performance, the addition of increasing amounts of TMAO had increasingly deleterious effects on the stability of the protein (see formulations 10-13).

Heat shock proteins are known in the art and are capable of stabilizing some biological systems from thermal stress (see for example Nakamoto, et al. in *Cell Mol Life Sci*. February; 64(3): 294-306 (2007)). Heat shock protein 70 was tested at levels of 0.1% and 0.2% w/v in a 60% trehalose solution with GDF-5 and showed acceptable results yielding 92% and 91% retention of the main peak, respectively.

Figure 1:
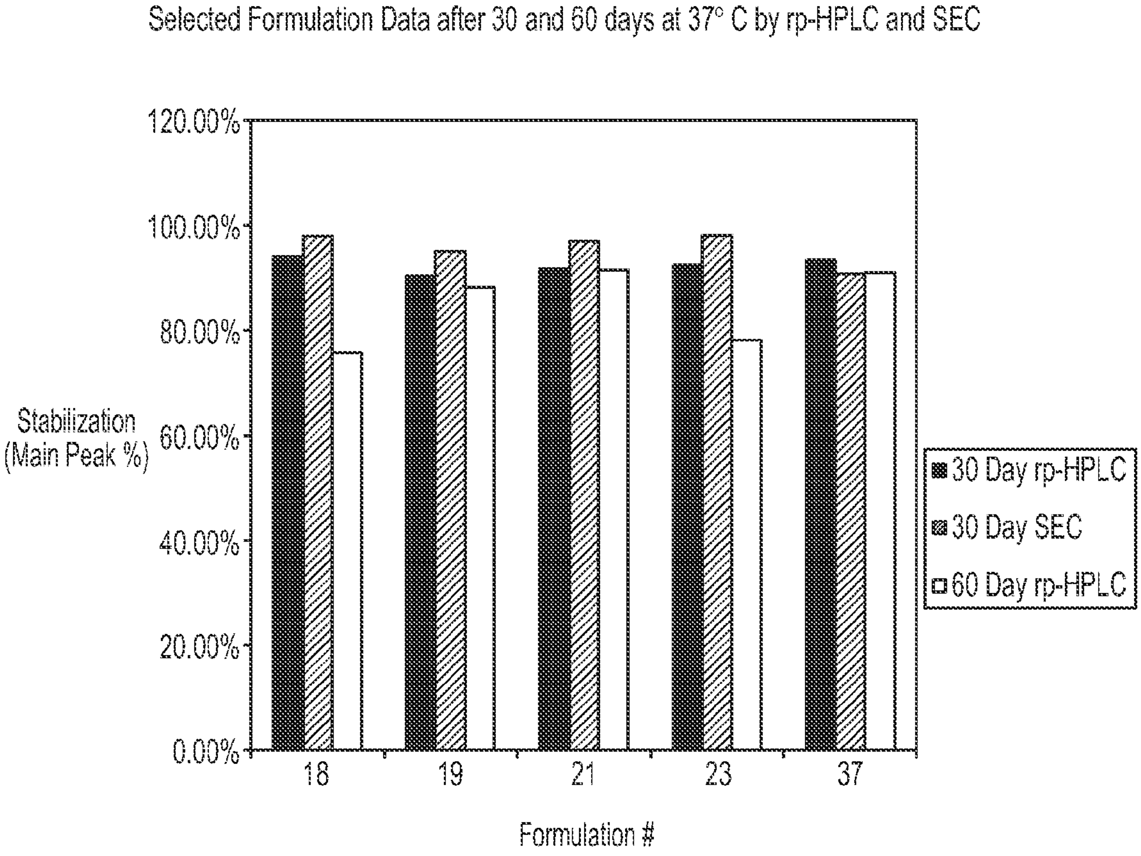
FIG. 1 shows the comparative stability of formulations #18, 19, 21, 23, and 37 by rp-HPLC after 30 and 60 days at 37° C. and also by SEC after 30 days at 37° C.
Figure 2:
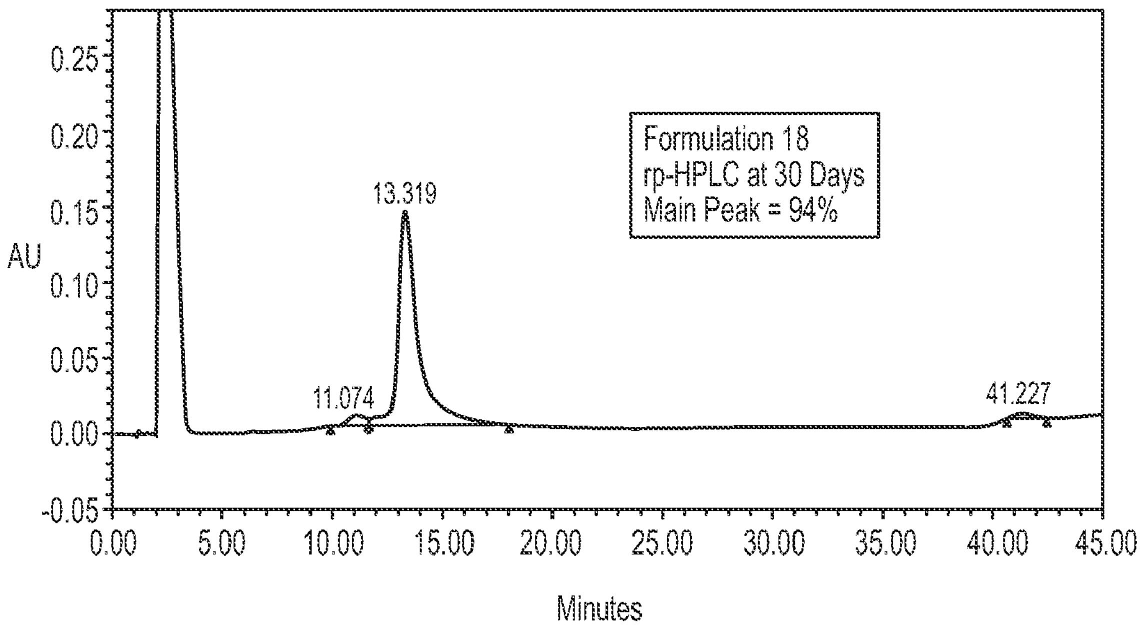
FIG. 2 shows the stability of formulation 18 by rp-HPLC after 30 days at 37° C. The preservation of the protein is shown to be 94% by the main peak and the absence of additional peaks.
Figure 3:
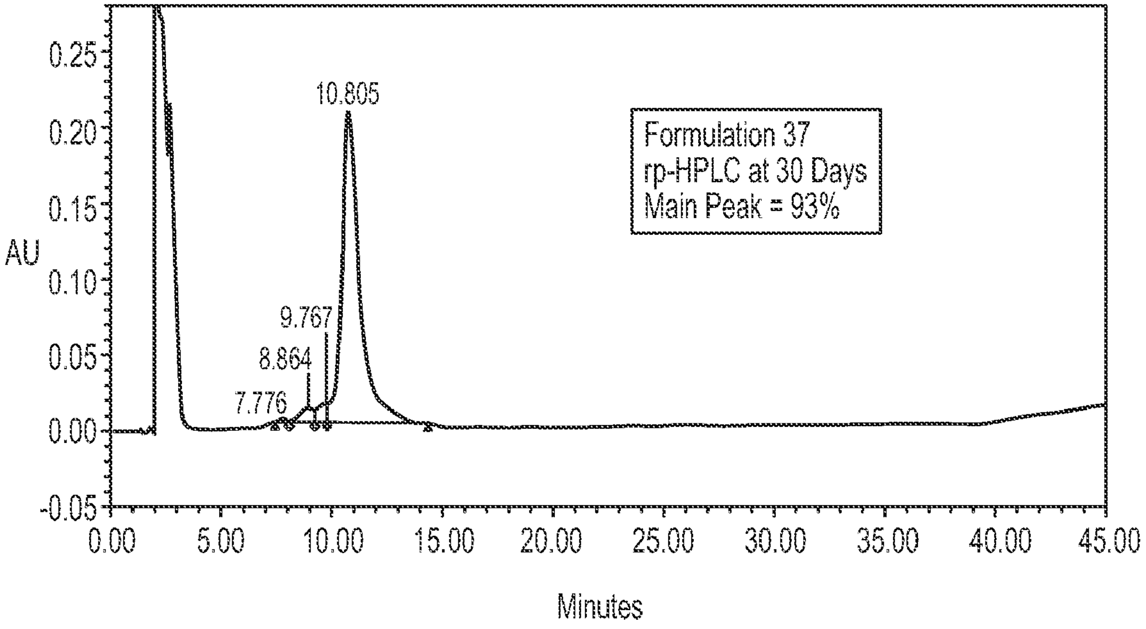
FIG. 3 shows the stability of formulation 37 by rp-HPLC after 30 days at 37° C. The preservation of the protein is shown to be 93% by the main peak and the absence of additional peaks.
Figure 4:
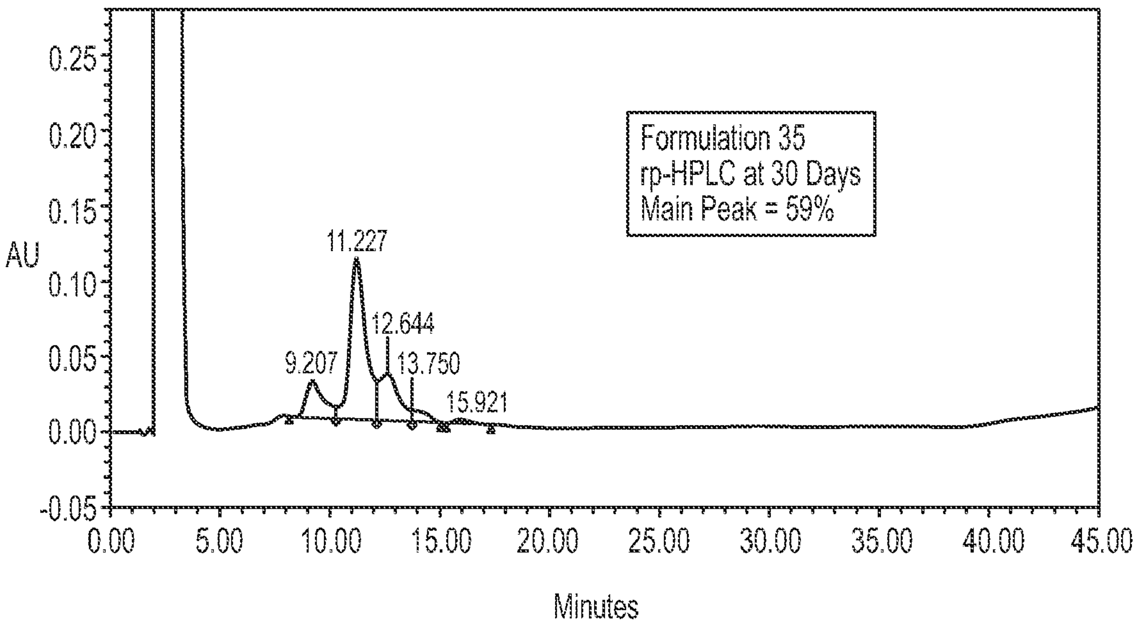
FIG. 4 shows the stability of formulation 35 by rp-HPLC after 30 days at 37° C. The preservation of the protein is shown to be 59% by the main peak, with the presence of additional peaks indicating degradation.
Figure 5:
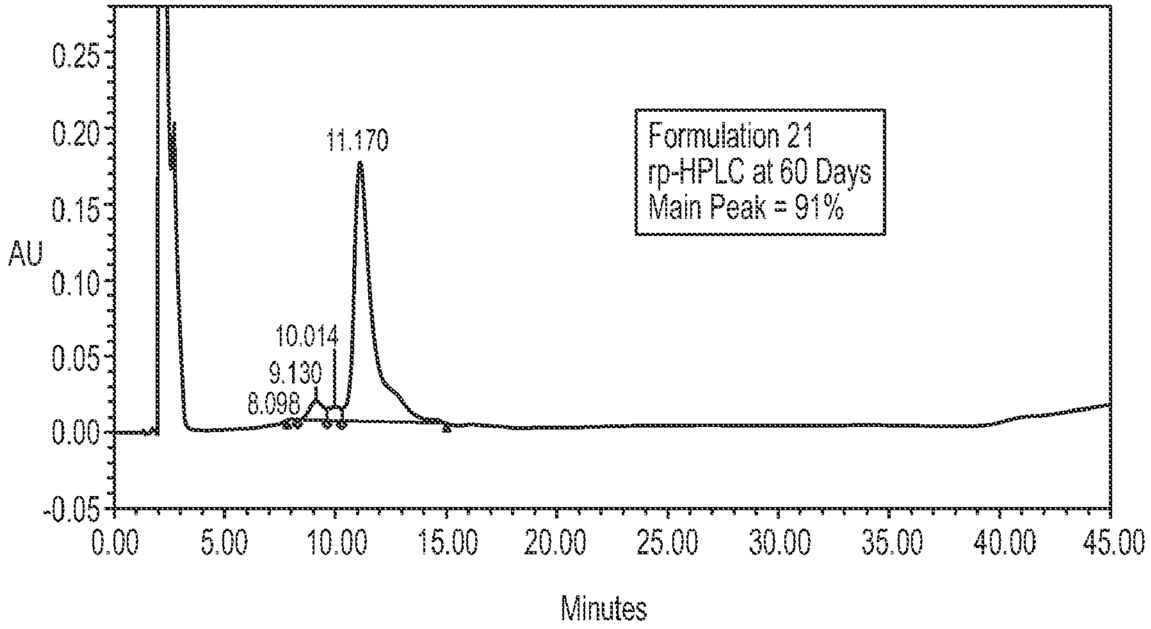
FIG. 5 shows the stability of formulation 21 by rp-HPLC after 60 days at 37° C. The preservation of the protein is shown to be 91% by the main peak and the absence of additional peaks.
Figure 6:
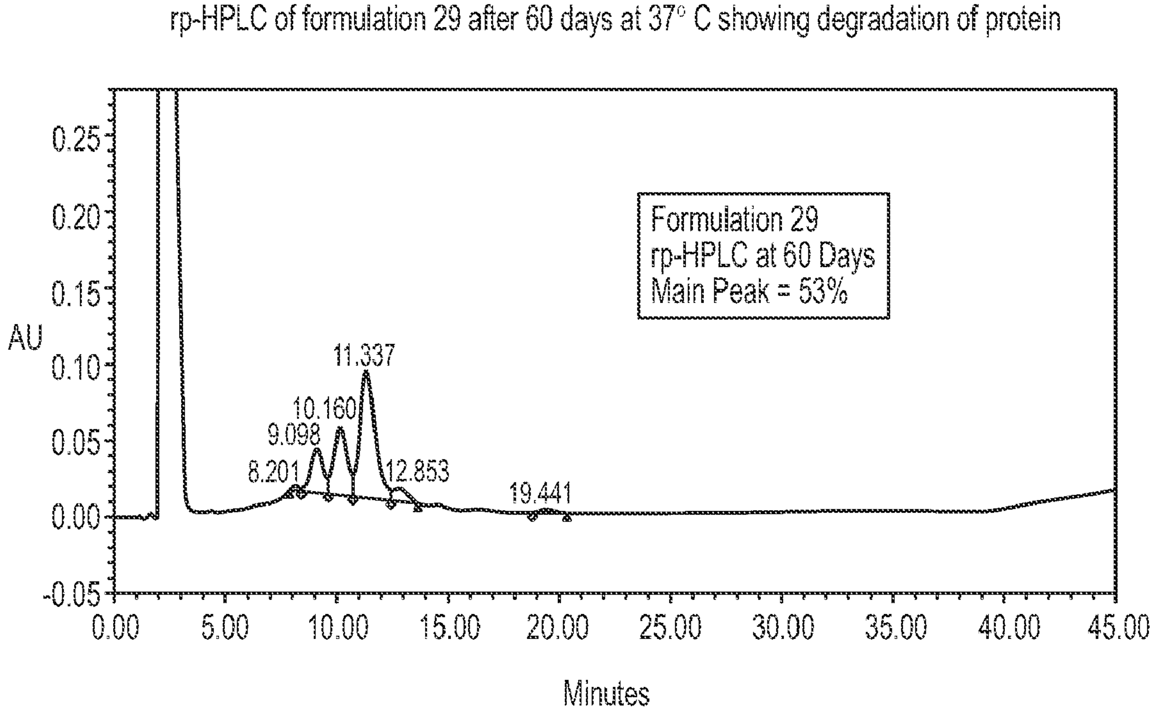
FIG. 6 shows the stability of formulation 29 by rp-HPLC after 60 days at 37° C. The preservation of the protein is shown to be 53% by the main peak, with the presence of additional peaks indicating degradation.
Figure 7:
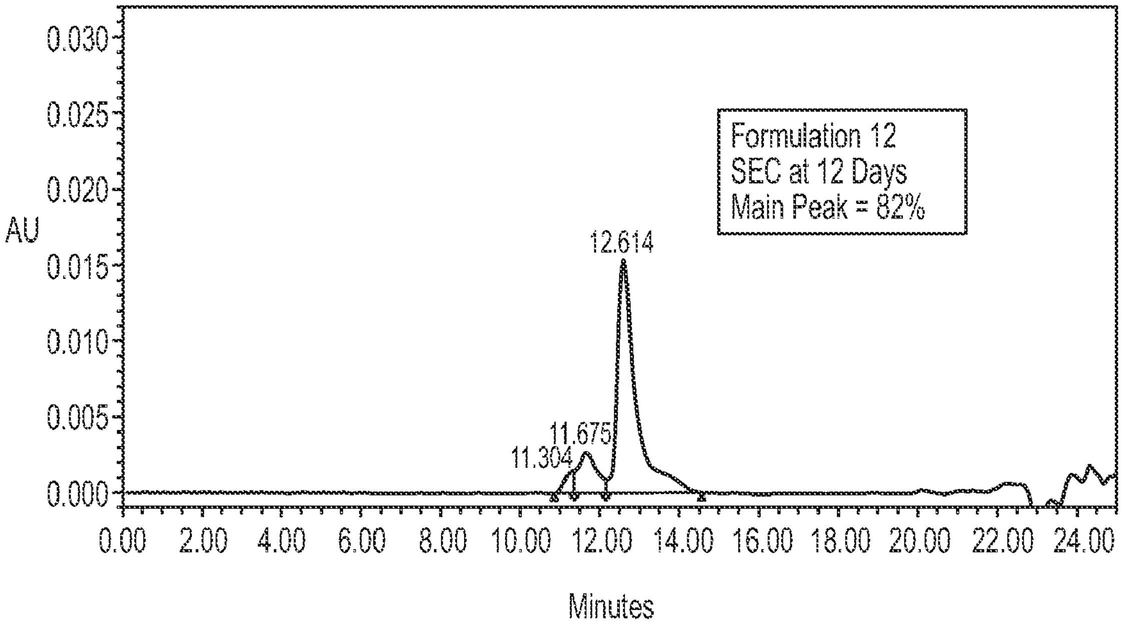
FIG. 7 shows the stability of formulation 12 by SEC after 12 days at 37° C. The preservation of the protein is shown to be 82% by the main peak, with the presence of a small additional peak indicating slight degradation.
Figure 8:
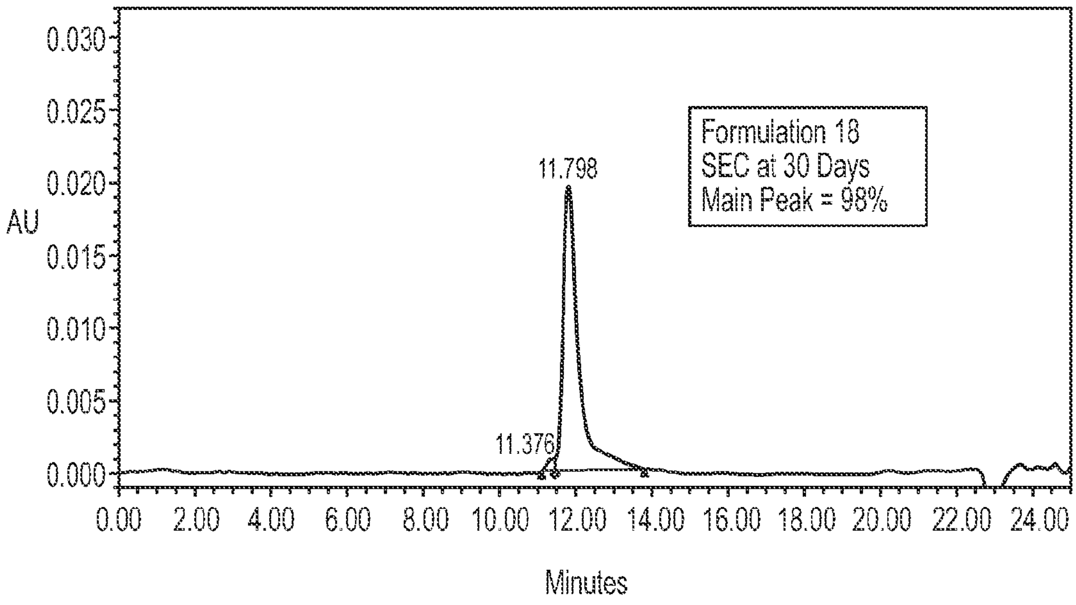
FIG. 8 shows the stability of formulation 18 by SEC after 30 days at 37° C. The preservation of the protein is shown to be 98% by the main peak and the absence of additional peaks.

Trimethylammonium hydrochloride (TMA) is a well-known excipient and was tested in conjunction with trehalose in several formulations at various concentrations, and also in conjunction with β-alanine. TMA provided satisfactory results in all formulations tested except formulation 36, which had a 50% trehalose solution. Due to the strong undesirable odor of TMA, triethylammonium hydrochloride (TEA) was investigated for its potential as a suitable substitute for TMA. Direct comparison of formulations 18 and 21 show that TEA is in fact a suitable substitute for TMA and provides for superior protein stabilization, as evidenced by FIGS. 2 and 5. In fact, FIG. 5 shows that formulation 21 with TEA provided the best overall long-term performance of all formulations tested, with 91% main peak retention after 60 days at 37° C.

A betaine is any neutral chemical compound with a positively charged cationic functional group such as an ammonium ion or phosphonium ion, and also has a negatively charged functional group such as a carboxyl group. These compounds exist as zwitterions and serve as organic osmolytes in biological systems, and are useful excipients. Historically, the term betaine has been reserved for the compound trimethylglycine after its discovery in sugar beets. Trimethylglycine hydrochloride is an exemplary betaine of the present invention, and has shown acceptable performance in several formulations at a 0.5% w/v level in conjunction with trehalose and other excipients (see formulations 23, 24, 28, and 32).

Amino acids are known to provide buffering capacity and are contemplated for use as excipients in the present invention. Examples of suitable amino acids include, but are not limited to isomers of alanine, glycine, proline, lysine, arginine, and histidine as exemplary amino acids useful as buffering agents. The amino acids may be used individually or in combination to provide buffering capacity. β-alanine was tested as an amino acid buffer in several formulations, and in general found to have beneficial properties. Formulations with trehalose and β-alanine provided acceptable results with β-alanine concentrations of 0.25% up to 2% w/v (formulations 14, 15 and 34), but not in 1% and 5% solutions (formulations 33 and 35). Formulation 19 included 0.5% β-alanine and 0.1% taurine and yielded excellent results, showing greater than 90% stability after 30 days at 37° C. by both rp-HPLC and SEC, and 88% stability after 60 days. Formulation 23 included 0.5% betaine, 1% TEA, and 0.5% each of L-Proline and potassium aspartate, and yielded excellent results after 30 days at 37° C., showing greater than 90% stability, but after 60 days had 78% stability. Other formulations utilizing L-proline and potassium aspartate that yielded acceptable results include formulations 24 and 28, yielding 82% and 83% respectively after 30 days at 37° C.

Figure 11:
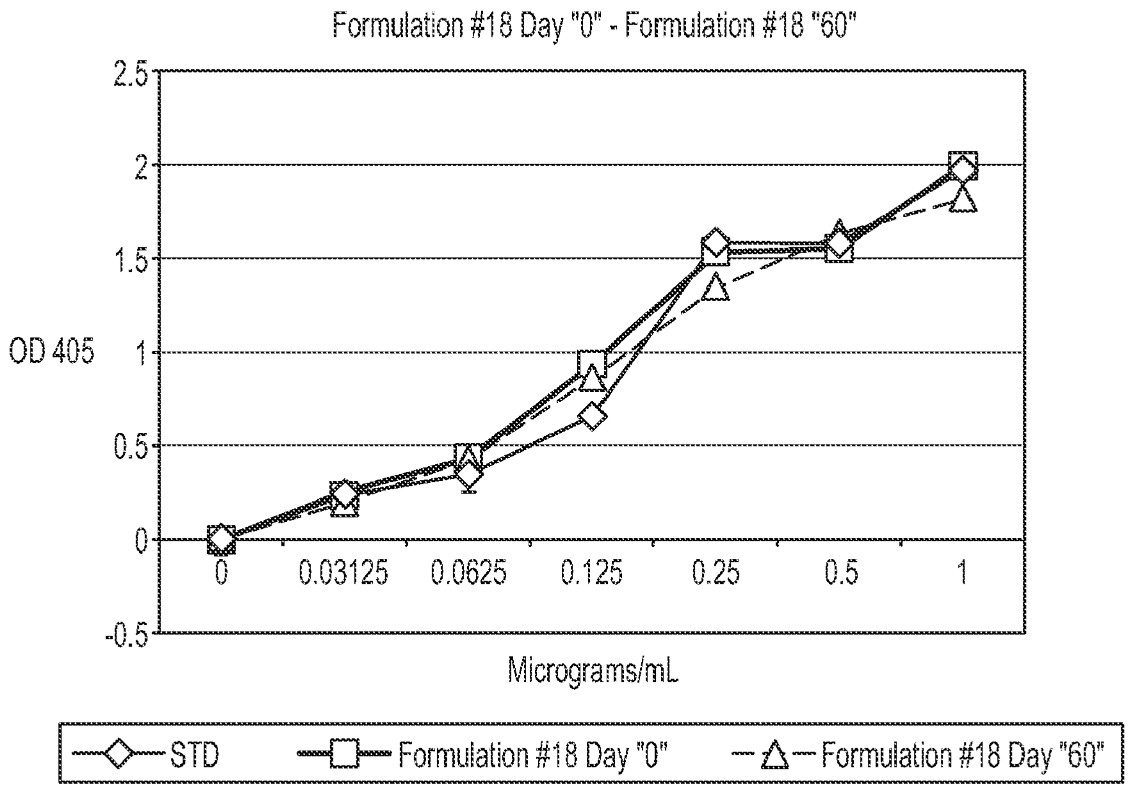
FIG. 11 shows the correlation between the activity of a freshly prepared GDF-5 standard solution, a freshly prepared solution of formulation #18, and a solution of formulation #18 after 60 days exposure to 37° C. The preservation of the activity of the protein is shown by the comparative similarity of the curves.

To confirm the correlation between the protein stability as demonstrated by the rp-HPLC main peak and the biological activity of the GDF-5 protein, formulation 18 was compared with a standard GDF-5 protein solution after exposing the formulation to 37° C. for 60 days, and also with the formulation at time zero. The biologic activity of GDF-5 was measured using different concentrations of GDF-5 on a bone marrow stromal cell line W-20-17. Increasing the amount of GDF-5 increased the Alkaline Phosphatase (ALP) in W-20-17, as was determined by a colorimetric assay. In FIG. 11 the ALP bioassay of formulation #18 at time zero and after 60 days at 37° C. were compared with a freshly prepared standard GDF-5 solution without excipients. All three curves exhibit similar profiles, indicating that the formulation does not reduce the activity at time zero, and that the formulation provides for an active protein after 60 days at 37° C.

In one embodiment, the present invention comprises a formulation of at least 50% w/v trehalose in an acidic solution, a BMP, and a trialkylammonium salt present in a concentration of from about 0.1% to about 5% w/v. In preferred embodiments the trialkylammonium salt can be trimethylammonium hydrochloride, triethylammonium hydrochloride, or a combination thereof, although one skilled in the art will appreciate that minor substitutions or modifications of the alkyl groups, the salt, or both the alkyl groups and salt would be considered equivalents of the present invention.

In another embodiment, the formulation comprises at least 50% w/v trehalose in an acidic solution, a BMP, and at least one amino acid present in an amount of from about 0.25% to about 5% w/v. In a preferred embodiment the at least one amino acid is β-alanine and is present in an amount of about 0.5% w/v. In another embodiment, the at least one amino acid is a combination of glycine and β-alanine, each present in an amount of from about 0.1% to about 2.5% w/v. In a preferred embodiment the β-alanine is present in an amount of about 0.25% and the glycine is present in an amount of about 0.25% w/v. In another embodiment the amino acid is a combination of L-glycine, L-proline, and L-alanine, each present in an amount of from about 0.1% to about 2.5% w/v.

In another embodiment the formulation comprises at least 50% w/v trehalose in an acidic solution, a BMP, and a heat shock protein present in an amount of from about 0.1% to about 0.2% w/v. In a preferred embodiment the heat shock protein is heat shock protein-70 and is present in an amount of about 0.1% w/v.

In another embodiment, the formulation comprises at least 50% w/v trehalose in an acidic solution, a BMP, β-alanine present in an amount of from about 0.25% to about 5% w/v, and taurine present in an amount of from about 0.01% to about 1% w/v. In a preferred embodiment the β-alanine is present in an amount of about 0.5% w/v and the taurine is present in an amount of about 0.1% w/v.

In another embodiment, the formulation comprises at least 50% w/v trehalose in an acidic solution, a BMP, β-alanine present in an amount of from about 0.25% to about 5% w/v, and a trialkylammonium salt present in an amount of from about 0.1% to about 5% w/v. In a preferred embodiment the β-alanine is present in an amount of about 0.5% w/v and the trialkylammonium salt is triethylammonium hydrochloride and is present in an amount of about 0.1% w/v.

In another embodiment, the formulation comprises at least 50% w/v trehalose in an acidic solution, a BMP, raffinose present in an amount of from about 1% to about 5% w/v, and myo-inositol present in an amount of from about 0.1% to about 3% w/v. In a preferred embodiment the raffinose is present in an amount of about 3% w/v and myo-inositol is present in an amount of about 1% w/v.

In another embodiment, the formulation comprises at least 50% w/v trehalose in an acidic solution, a BMP, β-alanine present in an amount of from about 0.25% to about 5% w/v, triethylammonium hydrochloride present in an amount of from about 0.1% to about 5% w/v, L-proline present in an amount of from about 0.1 to about 3% w/v, and potassium aspartate present in an amount of from about 0.1 to about 3% w/v. In a preferred embodiment the β-alanine is present in an amount of about 0.5% w/v, the triethylammonium hydrochloride is present in an amount of about 1% w/v, the L-proline is present in an amount of about 0.5% w/v, and the potassium aspartate is present in an amount of about 0.5% w/v.

The following examples illustrate some of the various embodiments and benefits of the present invention, however one skilled in the art will appreciate that other similar embodiments can be made without deviating from the scope and intent of the present invention.

EXAMPLES

Example 1

Preparation of Bulk Trehalose 60% w/v Solution 165.78 g of trehalose dihydrate (MW 378.34) were carefully weighed and transferred to a 250 ml size, clean volumetric flask, to which 1 mmol HCl was added slowly to just below the mark. The mixture was mixed thoroughly by shaking and warming in warm water at 60° C. The volume was brought to 250 ml by adding more 1 mmol HCl and letting all of the crystals completely dissolve; the solution was then filtered through a 0.2 um filter. This solution was used for the preparation of the formulations. In an analogous manner a 50% w/v solution was made for formulations 32 & 36 using a 50% trehalose solution.

Example 2

A non-limiting example of the preparation of a composition of the present invention is as follows (Formulation #19): 165.78 g of trehalose dihydrate (MW 378.34) were carefully weighed and transferred to a clean 250 ml volumetric flask, to which 1 mmol HCl was added slowly to just below the mark to produce a 60% w/v solution. The mixture was mixed thoroughly by shaking and warming in warm water at 60° C. The volume was brought to the mark by adding more 1 mmol HCl and ensuring that all of the trehalose crystals completely dissolved; the solution was then filtered through a 0.22 um filter. To 10 ml of the 60% trehalose solution, 51 mg of β-alanine and 10 mg of taurine were added. The mixture was swirled, to which 1000 ug (1 mg) of rhGDF-5 in solution was added. The protein concentration of the formulation was measured by UV light to ensure the desired concentration was achieved, and was adjusted by adding solvent or protein as needed.

Example 3

In a preferred embodiment, a formulation of the present invention is prepared as follows (Formulation #21): 165.78 g of trehalose dihydrate (MW 378.34) were carefully weighed and transferred to a 250 ml size, clean volumetric flask, to which 1 mmol HCl was added slowly to just below the mark to produce a 60% w/v solution. The mixture was mixed thoroughly by shaking and warming in warm water at 60° C. The volume was brought to the mark by adding more 1 mmol HCl and ensuring that all of the trehalose crystals were completely dissolved; the solution was then filtered through a 0.22 um filter. To 10 ml of the 60% trehalose solution, 50 mg of β-alanine and 10 mg of triethylamine hydrochloride (TEA) were added. The mixture was swirled, to which 1000 ug (1 mg) of rhGDF-5 in solution was added. The protein concentration of the formulation was measured by UV light to ensure the desired concentration was achieved, and was adjusted by adding solvent or protein as needed.

Example 4

In a preferred embodiment, a formulation of the present invention is prepared as follows (Formulation #32): 55.27 g of trehalose dihydrate (MW 378.34) were carefully weighed and transferred to a 100 ml size, clean volumetric flask, to which 1 mmol HCl was added slowly to just below the mark to produce a 50% w/v solution. The mixture was mixed thoroughly by shaking and warming in warm water at 60° C. The volume was brought to the mark by adding more 1 mmol HCl and ensuring that all of the trehalose crystals were completely dissolved; the solution was then filtered through a 0.22 um filter. To 10 ml of the 50% trehalose solution, 50 mg of betaine were added. The mixture was swirled, to which 1000 ug (1 mg) of rhGDF-5 in solution was added. The protein concentration of the formulation was measured by UV light to ensure the desired concentration was achieved, and was adjusted by adding solvent or protein as needed.

Materials and Equipment Used 1.1 Trehalose dihydrate, Ferro-Pfanstiehl #T-104-1-MC
1.2 Glycine, ultrapure grade, J. T. Baker #4059-00
1.3 β-alanine, 99%, Aldrich #239720
1.4 12 M HCl, EM Science #HX0603P/5 (concentrated stock reagent)
1.5 Trimethylamine N-Oxide Dihydrate (TMAO), Sigma #T0514
1.6 Trimethylammonium hydrochloride (TMA), 98%, Aldrich #T72761
1.7 Triethylammonium hydrochloride (TEA), Fluka #90350
1.8 Taurine, 99%, Sigma #T0625
1.9 Betaine, Sigma #B3501
1.10 Myo-inositol, 99% Sigma-Aldrich #15125
1.11 D-(+)-Raffinose Penta Hydrate, 98%, Sigma #R0250
1.12 HSP70, Sigma-Aldrich #H7283-1MG
1.13 Filtration units, 250 mL, 0.22 micron membrane, Nalgene #568-0020

1.14 Sterile, 250 mL, square PETG media bottles, Nalgene #2019-0250

1.15 UV-VIS spectrophotometer, Beckman-Coulter DU800, ID #494203

1.16 rhGDF-5: thawed at 2 to 8° C. prior to use 1.17 Water for injection, Baxter #2B0306

1.18 rp-HPLC: Waters model 2596, Vydac 218TP52, C18 column, eluted with 0.15% (v/v) TFA in water and 0.15% (v/v) TFA in acetonitrile at 0.3 ml/min. The eluted peaks were monitored at 214 nm.

1.19 SEC: Waters model 2596, TOSOH Bioscience, Cat #08540, eluted with 0.1% (v/v) TFA and 45% (v/v) acetonitrile in water at 0.5 ml/min. The protein peaks were monitored at 280 nm.

The formulations listed in table 1 were prepared in an analogous manner to the methods described in the examples above. The formulations were evaluated for their ability to stabilize the rhGDF-5 protein molecule over extended periods of time at elevated temperatures, as characterized by rp-HPLC and in some select samples also by SEC.

We claim:

1. A composition comprising GDF-5 and excipients in an acidic solution, wherein the excipients are trehalose present in the amount of 50% w/v-60% w/v, and at least one additional excipient selected from the group consisting of an amino acid, a trialkylammonium salt, a heat shock protein, a betaine, taurine, raffinose, myo-inositol, and potassium aspartate.

2. The composition of claim 1 wherein the amino acid is selected from the group consisting of β-alanine, L-glycine, and L-proline.

3. The composition of claim 2 wherein the amino acid is comprised of β-alanine present in an amount of from about 0.25% to about 5% w/v.

4. The composition of claim 3 wherein the β-alanine is present in an amount of about 0.5% w/v.

5. The composition of claim 1 wherein the trialkylammonium salt is present in an amount of from about 0.1% to about 3% w/v.

6. The composition of claim 5 wherein the trialkylammonium salt is triethylammonium hydrochloride.

7. The composition of claim 1 wherein the amino acid is present in an amount of from about 0.25% to about 5% w/v and the trialkylammonium salt is present in an amount of from about 0.1% to about 3% w/v.

8. The composition of claim 7 wherein the amino acid is β-alanine present in an amount of about 0.5% w/v and the trialkylammonium salt is triethylammonium hydrochloride present in an amount of about 0.1% w/v.

9. The composition of claim 1 wherein the heat shock protein is HSP 70 present in an amount of from about 0.1% to about 0.2% w/v.

10. The composition of claim 1 wherein the at least one additional excipient is comprised of β-alanine present in an amount of about 0.5% w/v and taurine present in an amount of about 0.1% w/v.

11. The composition of claim 1 wherein the at least one additional excipient is a betaine.

12. A method for stabilizing a GDF-5 solution comprising providing GDF-5 in an acidic solution, adding an amount of trehalose to provide 50% w/v-60% w/v solution of trehalose, and adding at least one additional excipient selected from the group consisting of an amino acid, a trialkylammonium salt, a heat shock protein, a betaine, taurine, raffinose, myo-inositol, and potassium aspartate.

* * * * *